US011692924B2

(12) United States Patent
Ono et al.

(10) Patent No.: US 11,692,924 B2
(45) Date of Patent: Jul. 4, 2023

(54) OPTICAL DEVICE AND METHOD FOR DETECTION TARGET SUBSTANCE ANALYSIS

(71) Applicant: JVCKENWOOD Corporation, Yokohama (JP)

(72) Inventors: Masayuki Ono, Yokohama (JP); Shigehiko Iwama, Yokohama (JP); Atsushi Saito, Yokohama (JP); Masahiro Yamamoto, Yokohama (JP); Yuichi Hasegawa, Yokohama (JP)

(73) Assignee: JVCKENWOOD CORPORATION, Yokohama (JP)

( * ) Notice: Subject to any disclaimer, the term of this patent is extended or adjusted under 35 U.S.C. 154(b) by 268 days.

(21) Appl. No.: 17/159,264

(22) Filed: Jan. 27, 2021

(65) Prior Publication Data

US 2021/0148808 A1 May 20, 2021

Related U.S. Application Data

(63) Continuation of application No. PCT/JP2019/022330, filed on Jun. 5, 2019.

(30) Foreign Application Priority Data

Aug. 1, 2018 (JP) .................. 2018-144673

(51) Int. Cl.
*G01N 15/14* (2006.01)
*G01N 15/00* (2006.01)

(52) U.S. Cl.
CPC . *G01N 15/1429* (2013.01); *G01N 2015/0065* (2013.01); *G01N 2015/1486* (2013.01)

(58) Field of Classification Search
CPC .................. G01N 15/1429; G01N 2015/1486
See application file for complete search history.

(56) References Cited

U.S. PATENT DOCUMENTS 10,060,847 B2 * 8/2018 Ling .................. G01N 15/1459
2003/0104486 A1 * 6/2003 Sei ....................... B01J 19/0046
506/3

(Continued)

FOREIGN PATENT DOCUMENTS

JP 2002-530786 A 9/2002
JP 2012-117882 A 6/2012

(Continued)

OTHER PUBLICATIONS

Dfficial Action dated Jan. 18, 2022 corresponding to Japanese application No. 2018-144673.

*Primary Examiner* — Rufus L Phillips
(74) *Attorney, Agent, or Firm* — Nath, Goldberg & Meyer; Jerald L. Meyer (57) ABSTRACT

An analysis device includes a controller configured to count a pulse derived from a particles as a plural particles when a light reception level signal includes the pulse having a first extreme value point, a second extreme value point, and a third extreme value point, and the pulse fulfils a condition in which the third extreme value point is present between the first extreme value point and the second extreme value point in a pulse width direction of the pulse, the third extreme value point is present between the first extreme value point and a threshold in a pulse amplitude direction, the first extreme value point and the second extreme value point are each an extreme value point of a waveform projecting in a common direction, and the third extreme value point is an extreme value point of a waveform in a direction opposite to the common direction.

6 Claims, 8 Drawing Sheets

(56) References Cited

U.S. PATENT DOCUMENTS

| | | | | |
|---|---|---|---|---|
| 2008/0221812 A1* | 9/2008 | Pittaro | ............... | G01N 15/14 |
| | | | | 702/66 |
| 2012/0133936 A1* | 5/2012 | Imai | ............... | G01N 15/1429 |
| | | | | 356/338 |
| 2017/0059485 A1* | 3/2017 | Yamamoto | ......... | G01N 15/1434 |
| 2017/0184582 A1* | 6/2017 | Ono | .............. | G01N 21/55 |

FOREIGN PATENT DOCUMENTS

| | | | |
|---|---|---|---|
| JP | 2015092148 A | * | 5/2015 |
| JP | 2017-207289 A | | 11/2017 |

\* cited by examiner

OPTICAL DEVICE AND METHOD FOR DETECTION TARGET SUBSTANCE ANALYSIS

CROSS REFERENCE TO RELATED APPLICATION

This application is a Continuation of PCT Application No. PCT/JP2019/022330, filed on Jun. 5, 2019, and claims the priority of Japanese Patent Application No. 2018-144673, filed on Aug. 1, 2018, the entire contents of both of which are incorporated herein by reference.

BACKGROUND

The present disclosure relates to an analysis device and an analysis method. More particularly, the present disclosure relates to an analysis device and an analysis method for analyzing biomaterials such as antigens and antibodies.

Immunoassays are known that quantitatively analyze disease detection and therapeutic effects by detecting particular antigens or antibodies associated with diseases as biomarkers. One of the immunoassays is an enzyme-linked immunosorbent assay (ELISA) for detecting antigens or antibodies labeled by enzymes, which is widely used because of having the advantage of low costs.

A technology using this method is known that causes particles for labeling detection target substances to be bound to the detection target substances that adhere to a surface of an optical disc provided with a tracking structure so that the particles are fixed to the optical disc, and detects a change in signal by an optical pickup (refer to JP 2002-530786 A). The state in which the particles are bound to the detection target substances having adhered to the optical disc can correspond to a state in which both the detection target substances and the particles are caused to be fixed to the optical disc.

SUMMARY

The device disclosed in JP 2002-530786 A generates pulse signals derived from the particles fixed to the optical disc as reflection signals received from the optical disc, so as to count the particles by use of the pulse signals. As described above, since the particles are bound to the detection target substances adhering to the optical disc, counting the particles can indirectly count the detection target substances.

The respective particles are not necessarily fixed to the optical disc in a state of being sufficiently separated from each other, but some of the particles are often fixed to the optical disc in state of aggregating adjacent to each other. Particularly when a sample of biomaterials containing a large amount of detection target substances is used, the number of particles fixed to the optical disc close to each other tends to be increased.

Since the pulse signals are generated close to each other when the particles are present close to each other, the pulse signals may interfere with each other. The interference between the respective pulse signals prevents the device from counting the particles accurately, which may impede a sufficient correspondence regarding the count result between the detection target substances and the particles. Conventional analysis devices and methods still need to be improved to have higher quantitative performance.

In view of the foregoing conventional problems, an object of the present disclosure is to provide an analysis device and an analysis method having high quantitative performance upon detecting particles present close to each other.

To solve the problems described above, an analysis device according to an aspect of the present disclosure includes an optical pickup configured to irradiate a sample analysis disc with an irradiation light, and receive a reflection light of the irradiation light from the sample analysis disc to generate a light reception level signal. The sample analysis disc has a surface to which detection target substances and particles bound to the detection target substances are fixed. The analysis device includes a controller configured to count a pulse derived from the particles as plural particles when the light reception level signal includes the pulse having a first extreme value point, a second extreme value point, and a third extreme value point, and the pulse fulfils a condition in which the third extreme value point is present between the first extreme value point and the second extreme value point in a pulse width direction of the pulse, the third extreme value point is present between the first extreme value point and a threshold in a pulse amplitude direction of the pulse, the first extreme value point and the second extreme value point are each an extreme value point of a waveform projecting in a common direction, and the third extreme value point is an extreme value point of a waveform projecting in a direction opposite to the common direction.

To solve the problems described above, an analysis method according to an aspect of the present disclosure includes an irradiation step of irradiating, with an irradiation light, a sample analysis disc having a surface to which detection target substances and particles bound to the detection target substances are fixed. The analysis method further includes a generation step of receiving a reflection light of the irradiation light from the sample analysis disc to generate a light reception level signal. The analysis method further includes a count step of counting a pulse derived from the particles as plural particles when the light reception level signal includes the pulse having a first extreme value point, a second extreme value point, and a third extreme value point, and the pulse fulfils a condition in which the third extreme value point is present between the first extreme value point and the second extreme value point in a pulse width direction of the pulse, the third extreme value point is present between the first extreme value point and a threshold in a pulse amplitude direction of the pulse, the first extreme value point and the second extreme value point are each an extreme value point of a waveform projecting in a common direction, and the third extreme value point is an extreme value point of a waveform projecting in a direction opposite to the common direction.

DETAILED DESCRIPTION

An analysis device and an analysis method according to the present embodiment are described in detail below. The dimensions of the elements in the drawings are exaggerated for illustration purposes, and are not necessarily drawn to scale.

[Detection Target Substance Capture Unit]

A detection target substance capture unit according to an embodiment is described below with reference to FIG. 1A to FIG. 3.

Figure 1A:
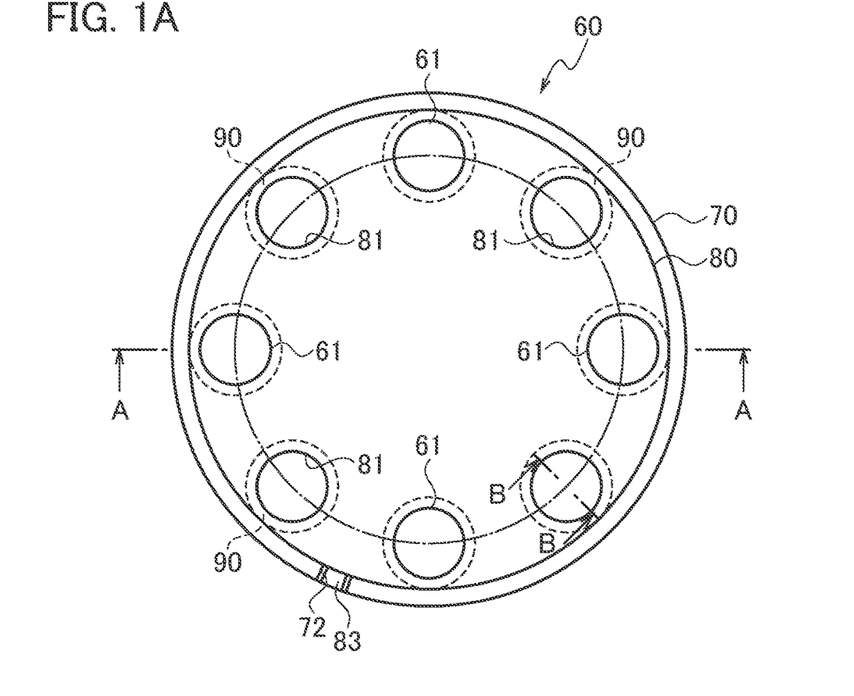
FIG. 1A is a plan view illustrating a detection target substance capture unit according to an embodiment as viewed from a surface provided with a cartridge.
Figure 1B:
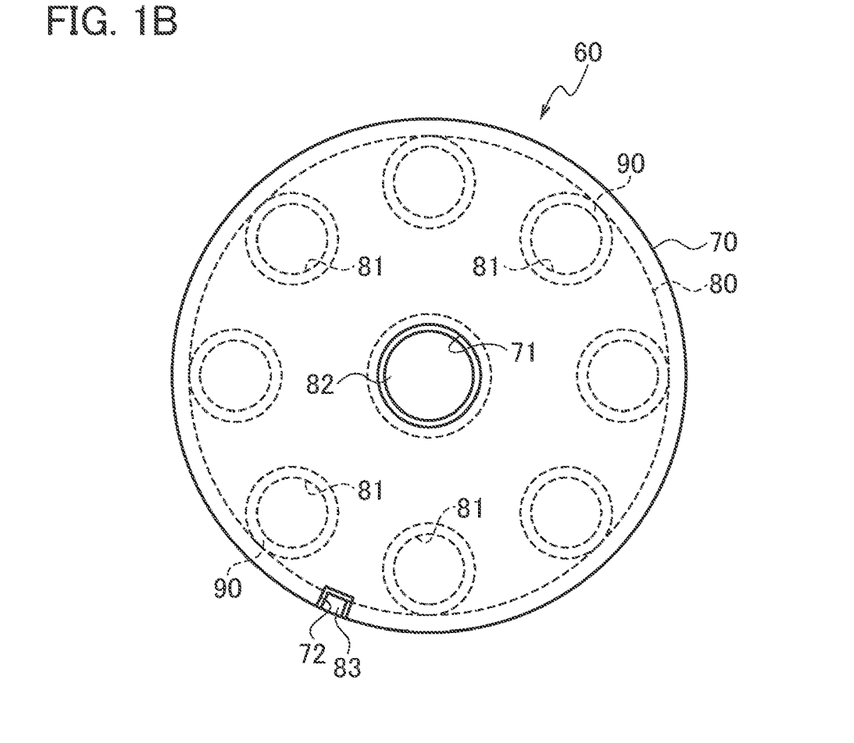
FIG. 1B is a plan view illustrating the detection target substance capture unit according to an embodiment as viewed from a surface provided with a sample analysis disc.
Figure 2A:
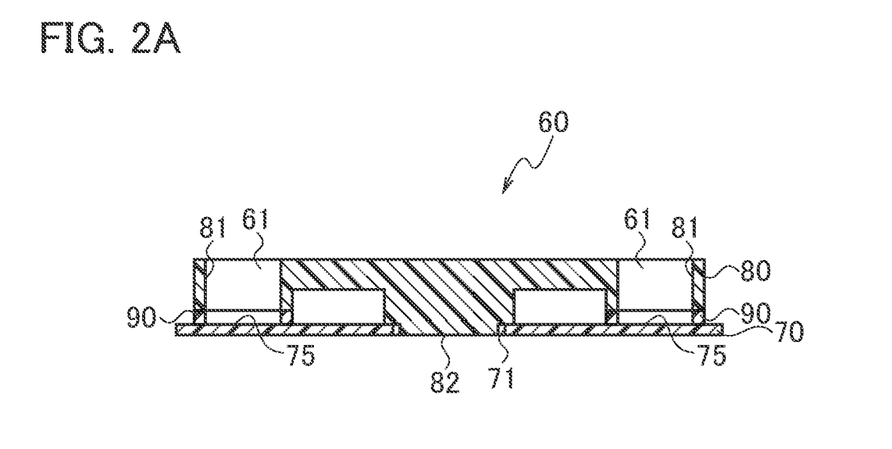
FIG. 2A is a cross-sectional view of the detection target substance capture unit taken along line A-A in FIG. 1A.
Figure 2B:
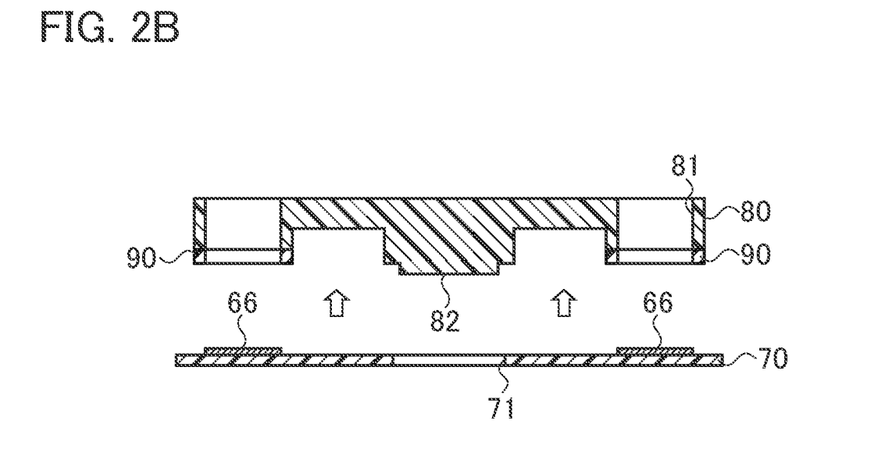
FIG. 2B is a cross-sectional view showing the cartridge that is removable from the sample analysis disc.
Figure 3:
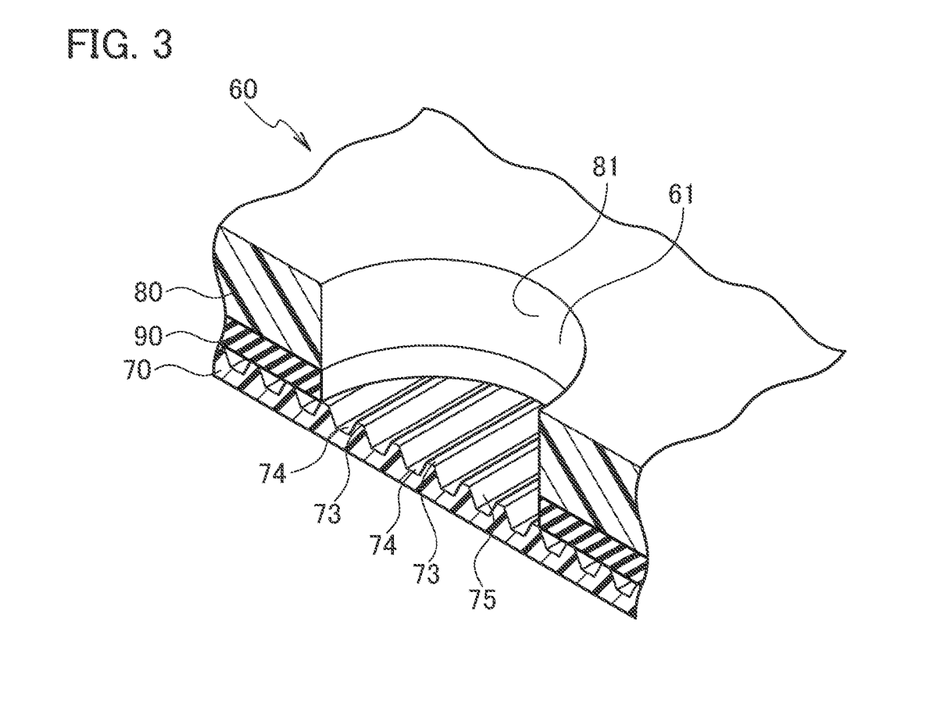
FIG. 3 is an enlarged perspective view showing a well cross-sectioned along line B-B in FIG. 1A.

FIG. 1A is a view showing the detection target substance capture unit 60 according to the embodiment as viewed from a surface provided with a cartridge 80. FIG. 1B is a view showing the detection target substance capture unit 60 as viewed from a surface provided with a sample analysis disc 70. FIG. 2A is a cross-sectional view of the detection target substance capture unit 60 taken along line A-A in FIG. 1A. FIG. 2B is a view showing the cartridge 80 that is removable from the sample analysis disc 70. FIG. 3 is a partly-enlarged view of a well cross-sectioned along line B-B in FIG. 1A.

As shown in FIG. 1A and FIG. 1B, the detection target substance capture unit 60 includes the sample analysis disc 70, the cartridge 80, and seal members 90.

The sample analysis disc 70 has a disc-like shape equivalent to optical discs such as Blu-ray discs (BDs), DVDs, and compact discs (CDs). The sample analysis disc 70 is formed of resin material, such as polycarbonate resin and cycloolefin polymer, used for common optical discs. The sample analysis disc 70 is not limited to the optical discs described above, and may be any optical disc according to other configurations or conforming to prescribed standards.

The sample analysis disc 70 has a central hole 71 in the middle, and a slit 72 provided at the circumferential edge thereof. The slit 72 serves as a reference-position defining portion for defining a reference position of the sample analysis disc 70.

As shown in FIG. 3, the surface of the sample analysis disc 70 has track regions 75 provided with convex portions 73 and recesses 74 alternately arranged in a radial direction. The convex portions 73 and the recesses 74 are formed in a spiral from the inner circumference to the outer circumference of the sample analysis disc 70. The convex portions 73 correspond to lands of an optical disc. The recesses 74 correspond to grooves of an optical disc. A track pitch of the recesses 74 which is a pitch in the radial direction is 320 nm, for example.

As shown in FIG. 1A, the cartridge 80 is provided with a plurality of cylindrical penetration holes 81 in the circumferential direction. The penetration holes 81 are arranged at regular intervals such that the respective centers are located on the common circle.

As shown in FIG. 1A, FIG. 1B, and FIG. 2B, the cartridge 80 is provided with a convex portion 82 (a first convex portion 82) in the middle, and a convex portion 83 (a second convex portion 83) at the circumferential edge.

As shown in FIG. 1B and FIG. 2A, when the cartridge 80 is attached to the sample analysis disc 70, the convex portion 82 is inserted into the central hole 71 of the sample analysis disc 70, and the convex portion 83 is inserted into the slit 72. The cartridge 80 and the sample analysis disc 70 are thus positioned together.

As shown in FIG. 2A, the seal members 90 are placed between the cartridge 80 and the sample analysis disc 70. The seal members 90 are ring-like gaskets formed of elastically-deformable material such as silicone rubber, for example. The seal members 90 are arranged along the respective penetration holes 81. The seal members 90 are elastically deformed to fill the recesses 74 of the track regions 75 when the cartridge 80 is attached to the sample analysis disc 70. FIG. 3 illustrates a state before the seal member 90 is elastically deformed.

As shown in FIG. 2A and FIG. 3, the detection target substance capture unit 60 includes a plurality of wells 61 defined by the penetration holes 81 of the cartridge 80, the seal members 90, and the track regions 75 of the sample analysis disc 70. The inner circumferential surfaces of the penetration holes 81 and the seal members 90 correspond to the inner circumferential surfaces of the wells 61, and the track regions 75 of the sample analysis disc 70 correspond to the bottoms of the respective wells 61. The wells 61 each serve as a holder for storing a solution such as a sample solution or a buffer solution. The seal members 90 can decrease a probability of leakage of the solution from the wells 61.

FIG. 1A illustrates the eight wells 61, but the number of the wells 61 is not limited to eight.

As shown in FIG. 2B, the cartridge 80, the seal members 90, and the sample analysis disc 70 are detachable from each other. The detection and measurement of particles that label detection target substances are made only by use of the sample analysis disc 70 separated from the cartridge 80 and the seal members 90.

[Formation of Reaction Regions]

Figure 4:
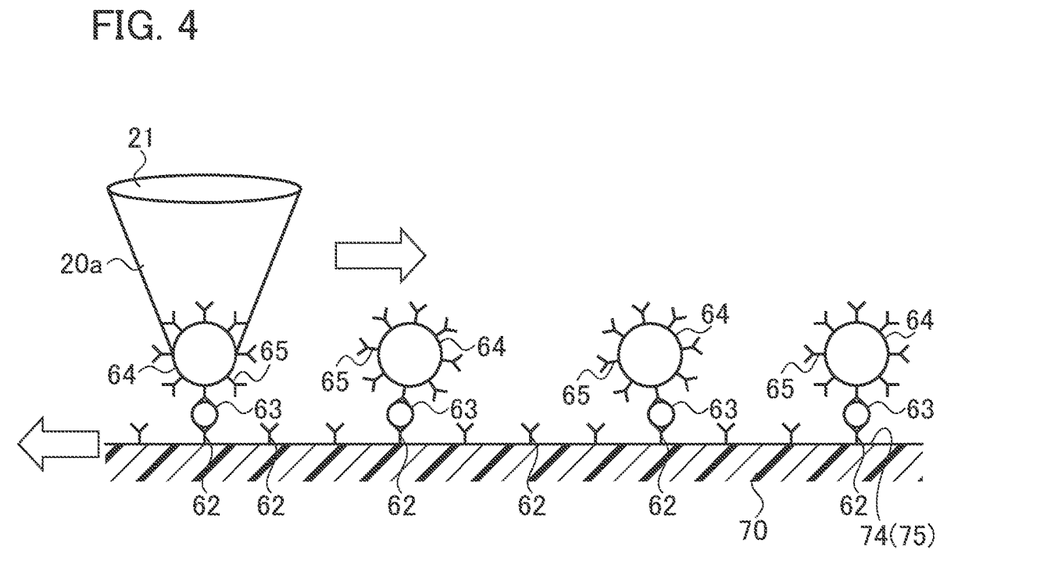
FIG. 4 is a schematic cross-sectional view showing a state in which detection target substances are captured and sandwiched between antibodies and particles in a recess of a track region.
Figure 5:
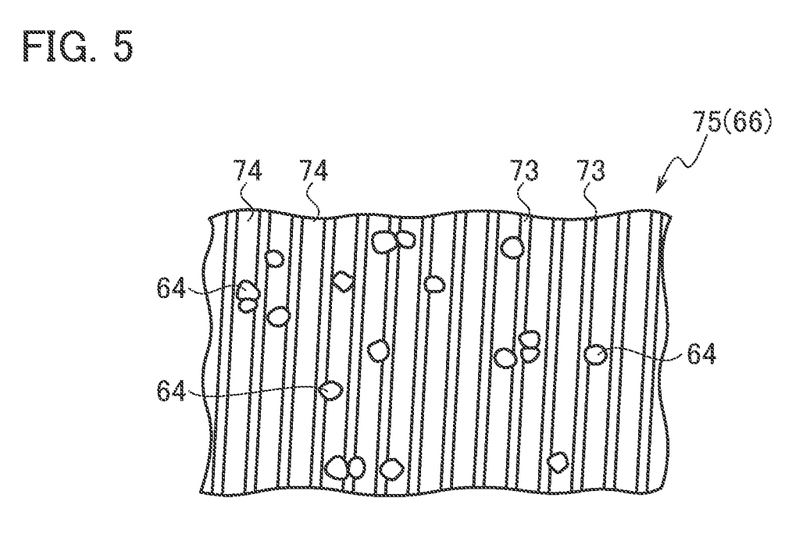
FIG. 5 is a schematic plan view showing a state in which the particles and the detection target substances bound together are captured in recesses of the track region.

A method of forming reaction regions 66 on the sample analysis disc 70 of the detection target substance capture unit 60 is described below with reference to FIG. 4 and FIG. 5.

A buffer solution including antibodies 62 is injected into the wells 61 of the detection target substance capture unit 60 and is then incubated. The antibodies 62 are thus fixed to the track regions 75 of the sample analysis disc 70 serving as the bottoms of the wells 61, as shown in FIG. 4. In the present embodiment, the antibodies 62 are first binding substances.

After the buffer solution is drained and the wells 61 are washed, a sample solution including detection target substances 63 (such as exosomes) which are antigens is injected into the wells 61 and is then incubated. The detection target substances 63 are specifically bound to the antibodies 62 by an antigen-antibody reaction. The detection target substances 63 are thus captured in the track regions 75, particularly in the recesses 74 of the track regions 75. The size of the exosomes that are the detection target substances 63 is about 100 nm.

After the sample solution is drained and the wells 61 are washed, a buffer solution including particles 64 serving as labels is injected to the wells 61 and is then incubated. Antibodies 65, which specifically bind to the detection target substances 63 by the antigen-antibody reaction, are fixed to the surfaces of the particles 64. In the present embodiment, the antibodies 65 are second binding substances. The size of the particles 64 is about 200 nm.

The particles 64 are captured in the recesses 74 of the track regions 75 in a state of being bound to the detection target substances 63. The detection target substances 63 are sandwiched between the antibodies 62 and the particles 64 and captured in the recesses 74 of the track regions 75 of the sample analysis disc 70. The detection target substances 63 and the particles 64 bound to the detection target substances 63 are fixed to the surface of the sample analysis disc 70 in the state of being captured in the recesses 74 of the track regions 75. FIG. 5 illustrates an example of the state in which the particles 64 bound to the detection target substances 63 are captured in the recesses 74 of the track region 75.

As shown in FIG. 2B, the cartridge 80 and the seal members 90 are removed from the sample analysis disc 70. The track regions 75 in the sample analysis disc 70 corresponding to the bottoms of the wells 61 are the reaction regions 66 on which the detection target substances 63 and the particles 64 are captured by the antibody-antigen reaction. Namely, the reaction regions 66 on which the particles 64 serving as labels are captured are formed in the respective wells 61.

[Analysis Device]

An analysis device according to an embodiment is described below with reference to FIG. 6.

The detection target substances 63, which are exosomes having a size as small as 100 nm, are hard to optically detect directly. The analysis device 1 detects and measures the particles 64 captured in the reaction regions 66 so as to indirectly detect and measure the detection target substances 63 specifically bound to the particles 64.

The analysis device 1 includes a turntable 2, a clamper 3, a turntable drive unit 4, a turntable drive circuit 5, a reference-position detection sensor 6, a guide shaft 7, an optical pickup 20, an optical pickup drive circuit 8, a controller 9, a storage unit 10, and a display unit 11. The analysis device 1 does not necessarily include the display unit 11, and an external display unit may be used instead.

The sample analysis disc 70 is placed on the turntable 2 with the reaction regions 66 facing down.

Figure 6:
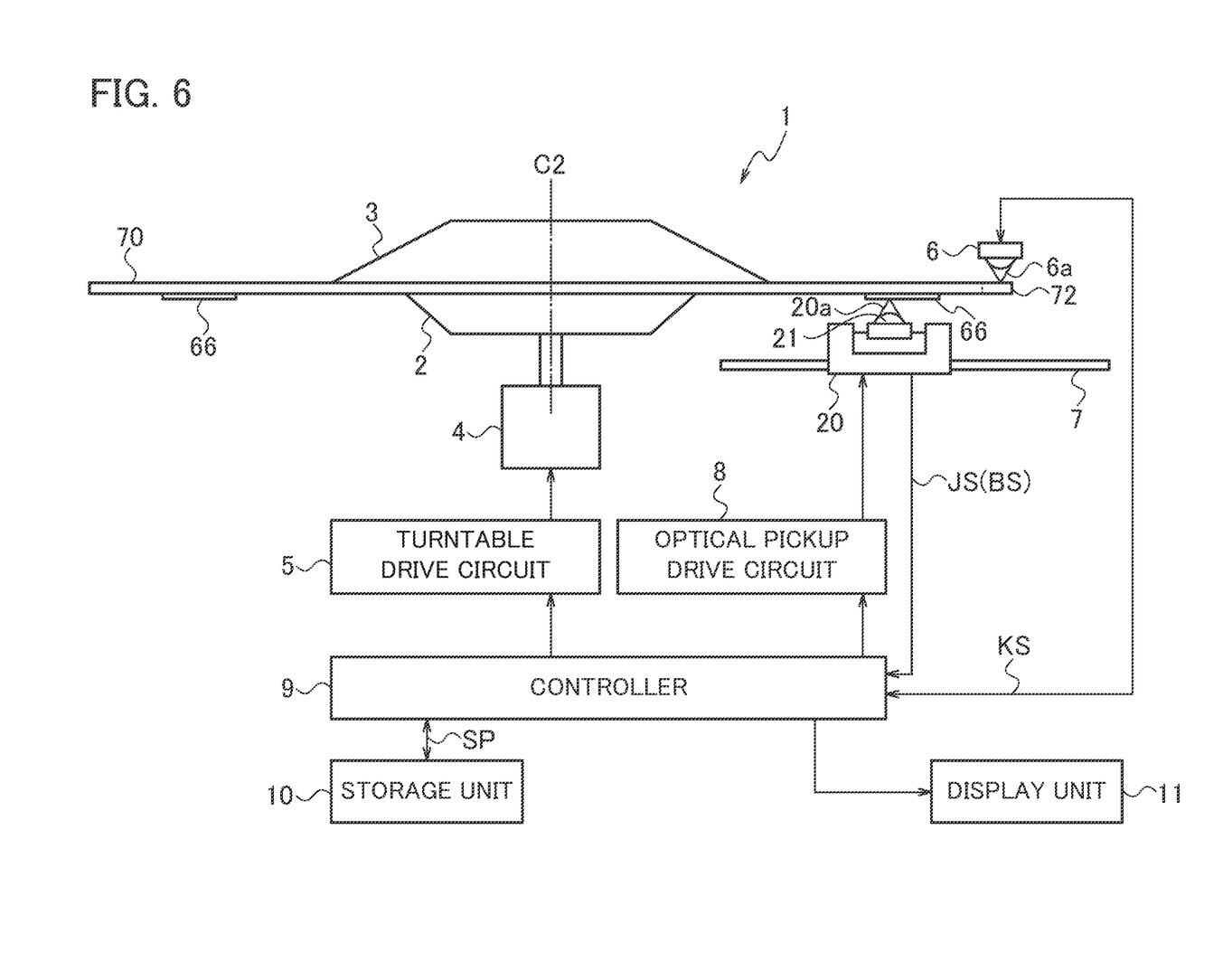
FIG. 6 is a configuration diagram illustrating an analysis device according to an embodiment.

The clamper 3 is driven in directions separating from and approaching the turntable 2, namely, in the upward and downward directions in FIG. 6. The sample analysis disc 70 is held by the clamper 3 and the turntable 2 when the clamper 3 is driven in the downward direction.

The turntable drive unit 4 drives the turntable 2 to rotate about the rotation axis C2 together with the sample analysis disc 70 and the clamper 3. A spindle motor may be used as the turntable drive unit 4.

The turntable drive circuit 5 controls the turntable drive unit 4. For example, the turntable drive circuit 5 controls the turntable drive unit 4 such that the turntable 2 rotates at a constant linear velocity together with the sample analysis disc 70 and the clamper 3.

The reference-position detection sensor 6 is placed adjacent to the outer circumferential portion of the sample analysis disc 70. The reference-position detection sensor 6 is an optical sensor such as a photoreflector, for example.

The reference-position detection sensor 6 emits detection light 6a toward the outer circumferential portion of the sample analysis disc 70 in a rotating state, and receives the reflected light from the sample analysis disc 70.

The reference-position detection sensor 6 detects the slit 72 of the sample analysis disc 70, generates a reference-position detection signal KS, and outputs the signal to the controller 9. The reference-position detection signal KS is a pulse signal that rises to be in an ON-state when the slit 72 reaches a detecting position 6b of the reference-position detection sensor 6, namely, a position irradiated with the detection light 6a, and falls to be in an OFF-state when the slit 72 passes through the detecting position 6b.

The reference-position detection sensor 6 detects the reference position per rotation period and per track of the sample analysis disc 70. A transmission-type optical sensor may be used as the reference-position detection sensor 6. The reference-position detection sensor 6 of this type irradiates the sample analysis disc 70 with the detection light 6a, and receives the detection light 6a passing through the slit 72, so as to detect the reference position per rotation period and per track of the sample analysis disc 70. The irradiation of the detection light 6a by the reference-position detection sensor 6 is controlled by the controller 9.

The guide shaft 7 is placed in parallel to the sample analysis disc 70 in the radial direction of the sample analysis disc 70.

The optical pickup 20 is supported by the guide shaft 7. The optical pickup 20 is driven along the guide shaft 7 in the direction perpendicular to the rotation axis C2 of the turntable 2, in the radial direction of the sample analysis disc 70, and in parallel to the sample analysis disc 70.

The optical pickup 20 includes an objective lens 21. As shown in FIG. 4 and FIG. 6, the optical pickup 20 irradiates the sample analysis disc 70 with irradiation light 20a such as laser light. The irradiation light 20a is condensed by the objective lens 21 on the track regions 75 provided with the reaction regions 66 on the sample analysis disc 70. The sample analysis disc 70 on which the particles 64 are captured in the recesses 74 of the track regions 75 by the antigen-antibody reaction, for example, is rotated at a constant linear velocity by the turntable 2. The optical pickup 20 is driven in the radial direction of the sample analysis disc 70 in the rotating state, so that the recesses 74 are optically scanned with the irradiation light 20a, as shown in FIG. 4.

The optical pickup 20 receives the reflected light of the irradiation light 20a from the sample analysis disc 70. The optical pickup 20 detects a light reception level of the reflected light, generates a light reception level signal JS, and outputs the signal to the controller 9.

The optical pickup drive circuit 8 controls the operation of the optical pickup 20. The optical pickup drive circuit 8 moves the optical pickup 20 along the guide shaft 7 or moves the objective lens 21 of the optical pickup 20 in the vertical direction.

The controller 9 controls the turntable drive circuit 5 and the optical pickup drive circuit 8. A central processing unit (CPU) may be used as the controller 9, for example.

The controller 9 controls the turntable drive circuit 5 to stop or rotate the turntable 2 at a constant linear velocity, for example. The controller 9 controls the turntable drive circuit 5 to cause the turntable drive unit 4 to rotate the turntable 2 so that the sample analysis disc 70 is rotated at a constant linear velocity.

The controller 9 controls the optical pickup drive circuit 8 to move the optical pickup 20 to a target position in the radial direction of the track regions 75. The controller 9 controls the optical pickup drive circuit 8 to adjust the position of the objective lens 21 in the vertical direction so that the optical pickup 20 emits the irradiation light 20*a* to the sample analysis disc 70 to condense the irradiation light 20*a* on the track regions 75.

The controller 9 detects the reference position per rotation period and per track of the sample analysis disc 70 in accordance with the reference-position detection signal KS output from the reference-position detection sensor 6. The controller 9 specifies the reaction regions 66 according to the reference position detected.

The storage unit 10 stores measurement parameters SP for every track. The measurement parameters SP include measurement information such as the number of the reaction regions 66, the time corresponding to the distance from the slit 72 as a reference-position defining portion to each reaction region 66, and the timing of measurement gate signals of each track.

The controller 9 reads out the measurement parameters SP from the storage unit 10, and sequentially generates a plurality of measurement gate signals for the respective reaction regions 66 based on the measurement parameters SP. The controller 9 extracts particle pulse signals BS per measurement gate signal from the light reception level signal JS output from the optical pickup 20.

The controller 9 counts the number of the particles 64 that label the detection target substances 63 based on the extracted particle pulse signals BS. The controller 9 adds the number of the particles 64 in the respective reaction regions 66 per track to store it in the storage unit 10. The controller 9 adds up the number of the particles 64 in each reaction region 66 and displays the sum on the display unit 11. The number of the particles 64 displayed corresponds to the number of the detection target substances 63. As described below, the controller 9 determines a pulse included in the light reception level signal JS as a pulse derived from the plural detection target substances 63 when including a first extreme value point PV1, a second extreme value point PV2, and a third extreme value point PM1. In the present specification, while the pulse signal is referred to also as a pulse waveform or simply referred to as a pulse, these are all the same meaning.

Figure 7:
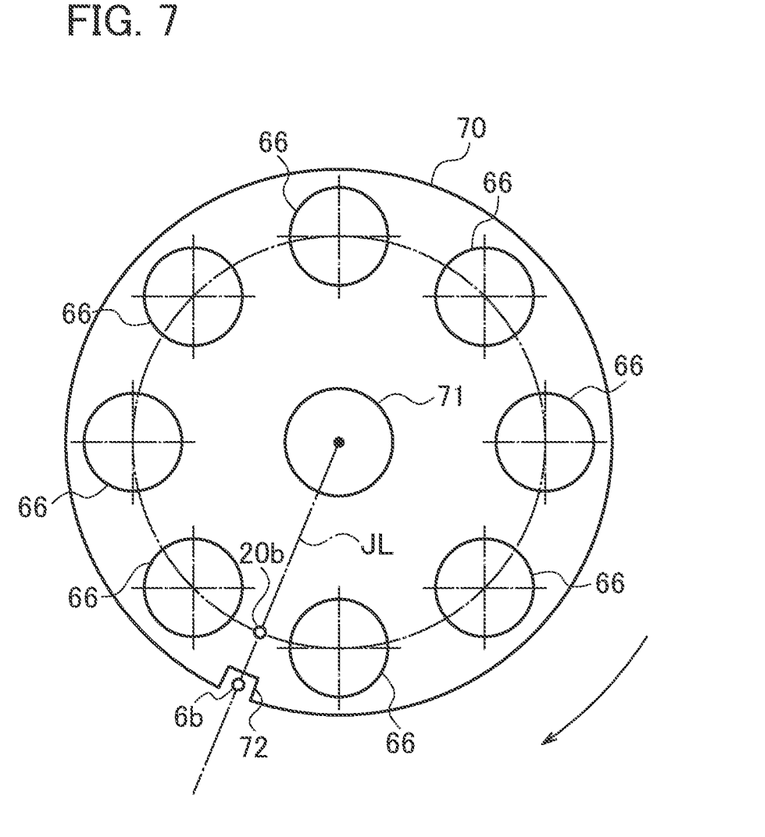
FIG. 7 is a plan view for explaining a positional relationship between detecting positions of a reference-position detection sensor and an optical pickup, and positions of a slit and reaction regions on the sample analysis disc.

FIG. 7 schematically illustrates a positional relationship between the detecting position 6*b* of the reference-position detection sensor 6, the detection position 20*b* of the optical pickup 20, and the positions of the slit 72 and the respective reaction regions 66 in the sample analysis disc 70.

As illustrated in FIG. 7, the sample analysis disc 70 is provided with the reaction regions 66 at the predetermined positions. The respective reaction regions 66 are arranged at regular intervals such that the respective centers are located on the common circle about the center of the sample analysis disc 70. The respective reaction regions 66 are located at the ideal positions predetermined on the sample analysis disc 70.

The optical pickup 20 moves along the axial line JL in the radial direction of the sample analysis disc 70. The axial line JL corresponds to the guide shaft 7. The detection position 20*b* of the optical pickup 20 is located so as to pass through the center of the respective reaction regions 66 on the common circle about the center of the sample analysis disc 70. The detecting position 6*b* of the reference-position detection sensor 6 is located on the axial line JL in FIG. 7, but is not limited to this illustration. The detecting position 6*b* may be any position at which the slit 72 can be detected at the circumferential edge of the sample analysis disc 70.

Figure 8:
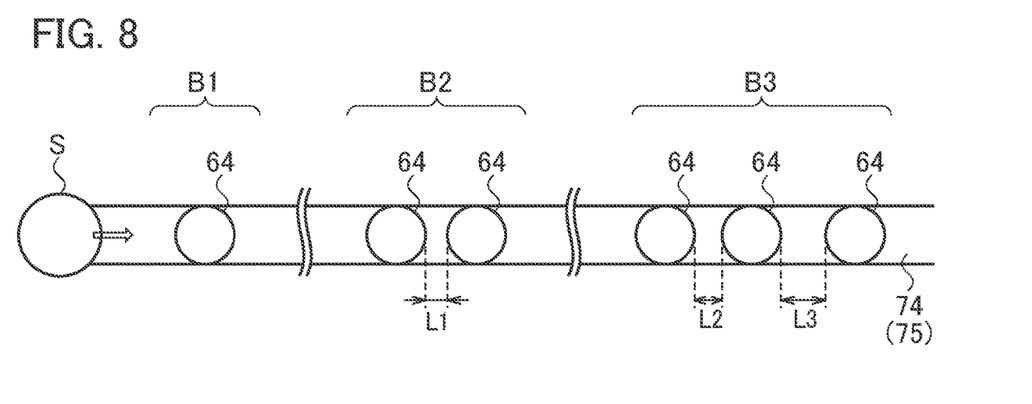
FIG. 8 is a plan view showing a state in which particles are captured in a recess of the track region.

FIG. 8 is a plan view showing a state in which the particles 64 are captured in the recess 74 of the track region 75. The optical pickup 20 emits the irradiation light 20*a* while scanning the recesses 74. The position irradiated with the irradiation light 20*a* is indicated by spot S. The reflection light of the irradiation light 20*a* is received by the optical pickup 20, and converted into the light reception level signal JS based on the intensity of the reflection light.

Figure 9:
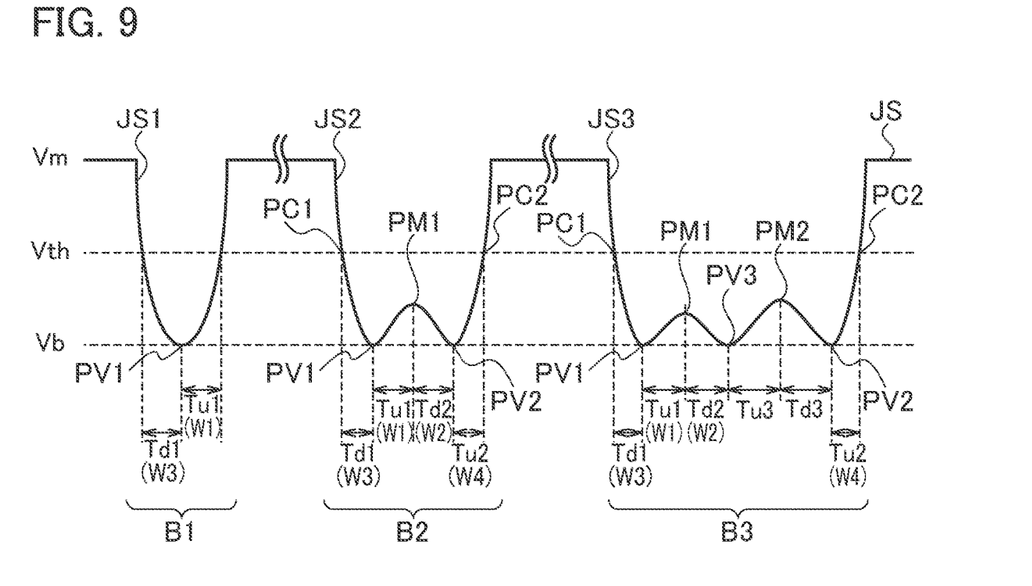
FIG. 9 is a diagram showing light reception level signals obtained by reflection of irradiation light emitted to the particles in the respective regions shown in FIG. 8.

FIG. 9 is a diagram showing the light reception level signals JS obtained by the reflection of the irradiation light 20*a* emitted to the particles 64 in the respective regions illustrated in FIG. 8. The scanning positions in FIG. 9 correspond to the scanning positions in FIG. 8, and FIG. 9 illustrates the light reception level signals JS corresponding to the respective scanning positions. While the present embodiment is illustrated with the case in which the pulses projecting downward are formed when the particles 64 are present, the pulses projecting upward may be formed when the particles 64 are present. The phrases "projecting upward" and "projecting downward" are used under the condition in which the amplitude direction of the pulses is defined as the vertical direction. The respective pulses "projecting upward" and "projecting downward" are thus opposite to each other in the pulse amplitude direction.

In the region B1 in FIG. 8 and FIG. 9, the single isolated particle 64 is captured in the recess 74. When the spot S scans the recess 74 in the region B1 as illustrated in FIG. 8, the light reception level signal JS1 is obtained as illustrated in FIG. 9. The light reception level signal JS1 forms a pulse with a substantially V-like shape having the extreme value point PV1 with a signal intensity of Vb. Since the pulse is a signal obtained upon the scanning by the optical pickup 20, the pulse width can be defined as a width in the time base direction, and the pulse amplitude can be defined in the intensity direction of the light reception level signal. In the present specification, the term "pulse width direction" refers to the time base direction, and the pulse amplitude direction refers to the intensity direction of the light reception level signal.

In the region B2 in FIG. 8 and FIG. 9, the two particles 64 are captured adjacent to each other with a gap L1 in the recess 74. When the spot S scans the recess 74 in the region B2 as illustrated in FIG. 8, the light reception level signal JS2 is obtained as illustrated in FIG. 9. The light reception level signal JS2 forms a pulse with a substantially W-like shape having the extreme value point PV1 and the extreme value point PV2 each having a signal intensity of Vb, and the extreme value point PM1 having a signal intensity of greater than Vb and less than Vth.

In the region B2 in FIG. 9, the pulse included in the light reception level signal JS2 includes the first extreme value point PV1, the second extreme value point PV2, and the third extreme value point PM1. The third extreme value point PM1 is present between the first extreme value point PV1 and the second extreme value point PV2 in the pulse width direction. The third extreme value point PM1 is present between the extreme value point PV1 and a threshold Vth in the pulse amplitude direction of the pulse. The first extreme value point PV1 and the second extreme value point PV2 are each an extreme value point of a waveform projecting downward, and the third extreme value point PM1 is an extreme value point of the waveform projection upward. The first extreme value point PV1 and the second extreme value point PV2 each may project upward, and the third extreme value point PM1 may project downward. In other words, the first extreme value point PV1 and the second extreme value point PV2 are each the extreme value point of one of the waveform projecting upward and the waveform projecting downward, and the third extreme value point PM1 is the extreme value point of the other one of the waveform projecting upward and the waveform projecting downward. As described below, the threshold Vth indicates a signal intensity having a predetermined level of intensity. According to the present embodiment, the threshold Vth can be set to a full width at half maximum of the pulse amplitude, but the specific value may be determined as appropriate. According to the present embodiment, the extreme value point is a point having an extreme value in which an inclination of a tangent is zero.

In the region B3 in FIG. 8 and FIG. 9, the three particles 64 are captured adjacent to each other with the respective gaps L2 and L3 in the recess 74. When the spot S scans the recess 74 in the region B3 as illustrated in FIG. 8, the light reception level signal JS3 is obtained as illustrated in FIG. 9. The light reception level signal JS3 forms a pulse having the first extreme value point PV1, the second extreme value point PV2, and a fourth extreme value point PV3 each having a signal intensity of Vb. The light reception level signal JS3 also forms a pulse having the extreme value point PM1 and an extreme value point PM2 each having a signal intensity of greater than Vb and less than Vth.

In the region B3 in FIG. 9, the pulse included in the light reception level signal JS3 includes the first extreme value point PV1, the second extreme value point PV2, the third extreme value point PM1, the fourth extreme value point PV3, and the fifth extreme value point PM2, which is similar to the region B2. The third extreme value point PM1 is present between the first extreme value point PV1 and the second extreme value point PV2 in the pulse width direction of the pulse. The fourth extreme value point PV3 is located between the third extreme value point PM1 and the second extreme value point PV2 in the pulse width direction of the pulse, and the fifth extreme value point PM2 is present between the second extreme value point PV2 and the fourth extreme value point PV3 in the pulse width direction of the pulse.

The third extreme value point PM1 and the fifth extreme value point PM2 are present between the first extreme value point PV1 and the threshold Vth in the pulse amplitude direction of the pulse. The first extreme value point PV1, the second extreme value point PV2, and the fourth extreme value point PV3 are each the extreme value point of the waveform projecting downward, and the third extreme value point PM1 and the fifth extreme value point PM2 are each the extreme value point of the waveform projection upward. The first extreme value point PV1 and the second extreme value point PV2 each may project upward, and the third extreme value point PM1 and the fifth extreme value point PM2 each may project downward. In other words, the first extreme value point PV1, the second extreme value point PV2 and the fourth extreme value point PV3 are each the extreme value point of one of the waveform projecting upward and the waveform projecting downward, and the third extreme value point PM1 and the fifth extreme value point PM2 are each the extreme value point of the other one of the waveform projecting upward and the waveform projecting downward.

When the single isolated particle 64 is captured in the recess 74 as in the case of the region B1, the light reception level signal JS1 obtained has a single extreme value point, and has a single peak having symmetry.

When the plural particles 64 are captured adjacent to each other in the recess 74 as in the case of the region B2 or the region B3, the light reception level signal JS2 and the light reception level signal JS3 obtained each form a pulse having a plurality of extreme value points with the same number as the particles 64 captured adjacent to each other. This phenomenon can also be observed in a case in which four or more particles 64 are captured adjacent to each other in the recess 74.

Figure 10:
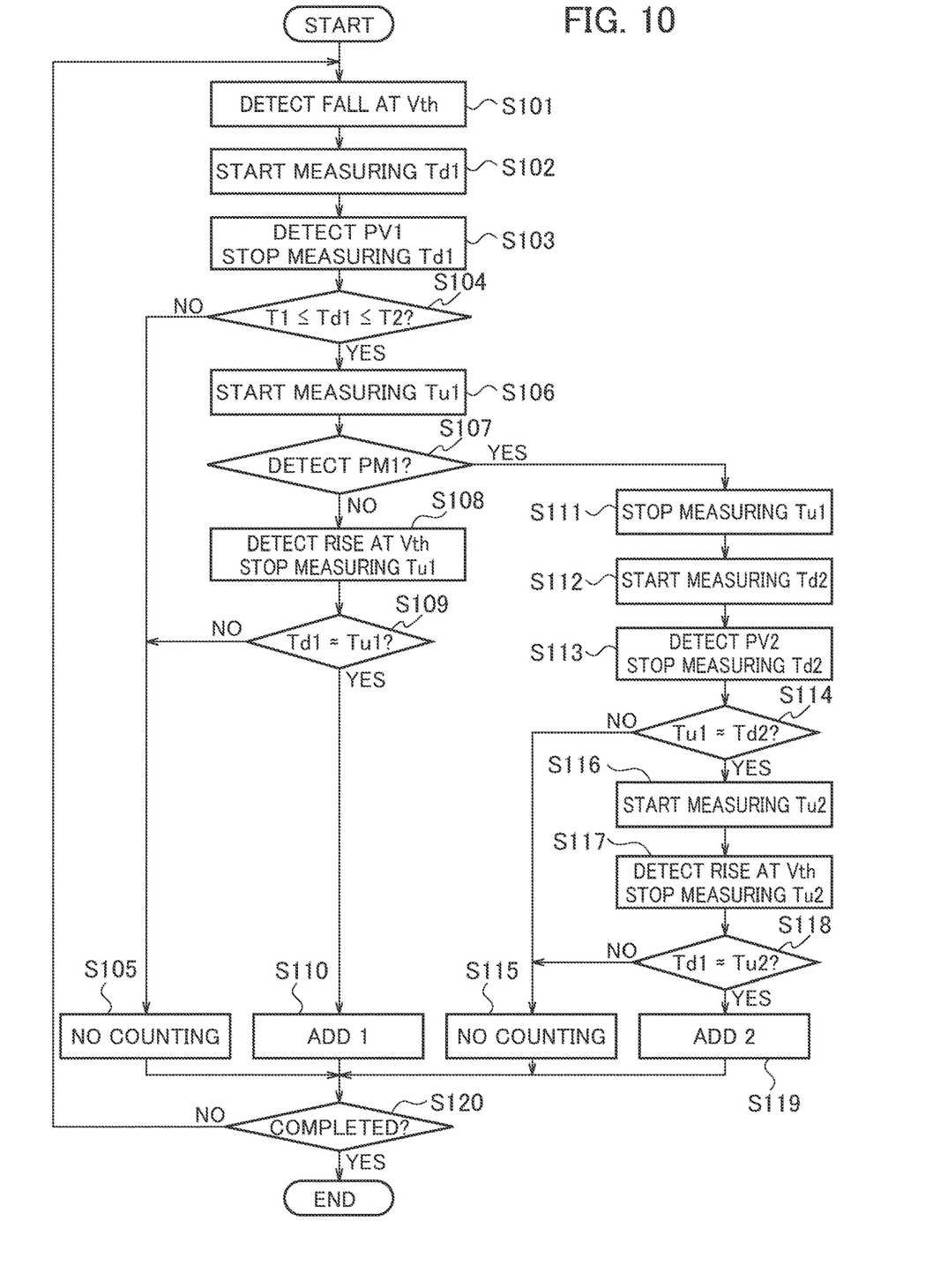
FIG. 10 is a flowchart showing an example of an analysis method according to the present embodiment.

A method of counting the particles 64 in the case in which the two particles 64 are captured adjacent to each other in the recess 74 as in the case of the region B2 is described below with reference to FIG. 9 and FIG. 10.

The controller 9 controls the turntable drive unit 4 and the optical pickup 20 via the turntable drive circuit 5 and the optical pickup drive circuit 8, respectively, so as to emit the irradiation light 20a while scanning the recess 74. The optical pickup 20 generates the light reception level signal JS based on the reflection light from the sample analysis disc 70.

In step S101, the controller 9 acquires the light reception level signal JS from the optical pickup 20, and detects the fall of the light reception level signal JS acquired. In the present embodiment, the controller 9 detects the fall when the signal intensity of the light reception level signal JS is the threshold Vth or smaller. While the threshold Vth is determined as appropriate, the present embodiment is illustrated with the case of Vth=(Vm−Vb)/2. The threshold Vth is preliminarily stored in a storage device in the controller 9, for example. The sign "Vm" refers to the signal intensity of the light reception level signal JS when none of the particles 64 or foreign matter is present on the sample analysis disc 70. The controller 9 then leads the process to proceed to step S102.

In step S102, the controller 9 starts measuring a time Td1 that the signal intensity of the light reception level signal JS takes to decrease from the threshold Vth to Vb. The controller 9 then leads the process to proceed to step S103.

In step S103, the controller 9 detects the extreme value point PV1. In particular, the controller 9 detects a point of change at which the signal intensity of the light reception level signal JS shifts from the fall to the rise as the extreme value point PV1. The controller 9 then stops measuring the time Td1 at the extreme value point PV1, and calculates and stores, as Td1, the time that the signal intensity of the light reception level signal JS takes to decrease from the threshold Vth to Vb at the extreme value point PV1. The controller 9 then leads the process to proceed to step S104.

In step S104, the controller 9 reads out a reference value T1 and a reference value T2 from the storage unit 10. The controller 9 determines whether the time Td1 stored in step S103 is T1 or greater and T2 or smaller. The controller 9 leads the process to step S105 when determining that the time Td1 is not T1 or greater and T2 or smaller (NO). The controller 9 leads the process to step S106 when determining that the time Td1 is T1 or greater and T2 or smaller (YES). The reference value T1 and the reference value T2 are each a time preliminarily obtained through a preliminary experiment, and can be changed as appropriate.

In step S105, the controller 9 determines that the pulse waveform is noise derived from foreign matter and aggregates, for example, and leads the process to proceed to step S120 while ignoring the pulse waveform without counting.

In step S120, the controller 9 determines whether scanning in a predetermined range is completed. When the scanning is completed (YES), the controller 9 ends the process and stops the measurement of the sample analysis disc 70. When the scanning is not completed yet (NO), the controller 9 returns the process to step S101.

In step S106, the controller 9 starts measuring a time Tu1 at the point at which the rise of the light reception level signal JS is detected in step S103. In particular, the controller 9 starts measuring the time Tu that the signal intensity takes to increase from the extreme value point PV1 to the threshold Vth. The controller 9 then leads the process to proceed to step S107.

In step S107, the controller 9 detects the extreme value point PM1. The extreme value point PM1 has the signal intensity of smaller than the threshold Vth in the light reception level signal JS, and is a point at which the light reception level signal JS shifts from the rise to the fall. The controller 9 leads the process to proceed to step S108 when determining that the light reception level signal JS does not have the extreme value point PM1 (NO). The controller 9 leads the process to proceed to step S111 when determining that the light reception level signal JS has the extreme value point PM1 (YES).

In step S108, the controller 9 stops measuring the time Tu1 at the threshold Vth when the fall of the light reception level signal JS is not detected from the extreme value point PV1 but the signal intensity reaches the threshold Vth. The controller 9 calculates and stores, as Tu1, the time that the signal intensity of the light reception level signal JS takes to increase from Vb at the extreme value point PV1 to the threshold Vth. The controller 9 then leads the process to proceed to step S109.

In step S109, the controller 9 compares Td1 stored in step S103 with Tu1 stored in step S108. The controller 9 then determines whether Td1 and Tu1 conform to each other. The controller 9 leads the process to proceed to step S105 when determining that Td1 and Tu1 do not conform to each other (NO). The controller 9 leads the process to proceed to step S110 when determining that Td1 and Tu1 conform to each other (YES). When Td1 and Tu1 are determined to conform to each other, the light reception level signal JS is presumed to include the single isolated particle 64 captured in the recess 74, as in the case of the region B. However, Td1 and Tu1 sometimes do not completely conform to each other since the light reception level signal JS has a jitter value. In view of this, the controller 9 may determine that Td1 and Tu1 conform to each other when the rate of Tu1 to Td1 is in a range of 85% to 115%.

In step S110, the controller 9 determines that the pulse waveform indicates the single isolated particle 64 and adds 1 to the count number, and then leads the process to proceed to step S120.

In step S111, the controller 9 stops measuring the time Tu1 at the extreme value point PM1, and calculates and stores, as Tu1, the time that the signal intensity of the light reception level signal JS takes to shift from the extreme value point PV1 to the extreme value point PM1 detected in step S107. The controller 9 then leads the process to proceed to step S112.

In step 112, the controller 9 starts measuring a time Td2 at the point at which the fall of the light reception level signal JS is detected in step S107. Namely, the controller 9 starts measuring the time Td2 from the extreme value point PM1. The controller 9 then leads the process to proceed to step S113.

In step S113, the controller 9 detects the extreme value point PV2. In particular, the controller 9 detects a point of change at which the signal intensity of the light reception level signal JS shifts from the fall to the rise as the extreme value point PV2 after the extreme value point PM1. The controller 9 then stops measuring the time Td2 at the extreme value point PV2, and calculates and stores, as Td2, the time between the extreme value point PM1 to the extreme value point PV2. The controller 9 then leads the process to proceed to step S114.

In step S114, the controller 9 compares Tu1 stored in step S111 with Td2 stored in step S113. The controller 9 determines whether Tu1 and Td2 conform to each other. The controller 9 leads the process to proceed to step S115 when determining that Tu1 and Td2 do not conform to each other (NO). The controller 9 leads the process to proceed to step S116 when determining that Tu1 and Td2 conform to each other (YES). When Tu1 and Td2 are determined to conform to each other, the light reception level signal JS is presumed to include the two particles 64 captured adjacent to each other with a predetermined distance in the recess 74, as in the case of the region B2. However, Tu1 and Td2 sometimes do not completely conform to each other since the light reception level signal JS has a jitter value. In view of this, the controller 9 may determine that Tu1 and Td2 conform to each other when the rate of Td2 to Tu1 is in a range of 85% to 115%.

The time Tu1 and the time Td2 can be replaced with a first width W1 and a second with W2, since the measurement time of the pulse is proportional to the width of the pulse. In the present embodiment, the third extreme value point PM1 may be an extreme value point adjacent to the first extreme value point PV1. The controller 9 may determine that the time Tu1 and the time Td2 conform to each other when a difference between the first width W1 and the second width W2 in the pulse width direction is 15% or less of either the first width W1 or the second width W2 having a greater value. The first width W1 is a width between the first extreme value point PV1 and the third extreme value point PM1. The second width W2 is a width between the third extreme value point PM1 and the extreme value point adjacent to the third extreme value point PM1 on the opposite side of the first extreme value point PV1. When the two particles 64 adjacent to each other are captured in the recess 74, the extreme value point adjacent to the third extreme value point PM1 on the opposite side of the first extreme value point PV1 is the second extreme value point PV2.

In step S115, the controller 9 determines that the pulse waveform is noise derived from foreign matter and aggregates, for example, and leads the process to proceed to step S120 while ignoring the pulse waveform without counting.

In step S116, the controller 9 starts measuring a time Tu2 at the point at which the rise of the light reception level signal JS is detected in step S113. Namely, the controller 9 starts measuring the time Td2 from the extreme value point PV2 detected in step S113. The controller 9 then leads the process to proceed to step S117.

In step S117, the controller 9 stops measuring the time Tu2 when the signal intensity shifts from V b at the extreme value point PV2 to reach the threshold Vth. The controller 9 calculates and stores, as Tu2, the time that the signal intensity of the light reception level signal JS takes to increase from Vb at the extreme value point PV2 to the threshold Vth. The controller 9 then leads the process to proceed to step S118.

In step S118, the controller 9 compares Td1 stored in step S103 with Tu2 stored in step S117. The controller 9 then determines whether Td1 and Tu2 conform to each other. The controller 9 leads the process to proceed to step S115 when determining that Td1 and Tu2 do not conform to each other (NO). The controller 9 leads the process to proceed to step S119 when determining that Td1 and Tu2 conform to each other (YES). When Td1 and Tu2 are determined to conform to each other, the light reception level signal JS is presumed to include the two particles 64 captured adjacent to each other with a predetermined distance in the recess 74, as in the case of the region B2. However, Td1 and Tu2 sometimes do not completely conform to each other since the light reception level signal JS has a jitter value. In view of this, the controller 9 may determine that Td1 and Tu2 conform to each other when the rate of Tu2 to Td1 is in a range of 85% to 115%.

The time Td1 and the time Tu2 can be replaced with a third width W3 and a fourth with W4, since the measurement time of the pulse is proportional to the width of the pulse. In the present embodiment, the first extreme value point PV1 may be an extreme value point present at a position closest to a first intersection PC1 of the pulse with the threshold Vth toward the first extreme value point PV1 based on the third extreme value point PM1. The second extreme value point PV2 may be an extreme value point present at a position closest to a second intersection PC2 of the pulse with the threshold Vth on the opposite side of the first extreme value point PV1 based on the third extreme value point PM1. A difference between the third width W3 and the fourth with W4 in the pulse width direction may be 15% or less of either the third width W3 or the fourth with W4 having a greater value. The third width W3 is a width between the first intersection PC1 and the first extreme value point PV1. The fourth width W4 is a width between the second intersection PC2 and the second extreme value point PV2.

In step S119, the controller 9 determines that the pulse waveform indicates the two particles 64 adjacent to each other and adds 2 to the count number, and then leads the process to proceed to step S120.

As described above, the analysis device 1 according to the present embodiment includes the optical pickup 20 that irradiates the sample analysis disc 70 with the irradiation light 20a, and receives the reflection light of the irradiation light 20a from the sample analysis disc 70 to generate the light reception level signal JS. The detection target substances 63 and the particles 64 bound to the detection target substances 63 are fixed to the surface of the sample analysis disc 70. The analysis device 1 includes the controller 9 that determines and counts the pulse as a pulse derived from the plural detection target substances 63 when fulfilling the following conditions. The pulse included in the light reception level signal JS includes the first extreme value point PV1, the second extreme value point PV2, and the third extreme value point PM1, in which the third extreme value point PM1 is present between the first extreme value point PV1 and the second extreme value point PV2 in the pulse width direction of the pulse. The third extreme value point PM1 is present between the first extreme value point PV1 and the threshold Vth in the pulse amplitude direction of the pulse. The first extreme value point PV1 and the second extreme value point PV2 are the extreme value points of one of the waveform projecting upward and the waveform projecting downward, and the third extreme value point PM1 is the extreme value point of the other one of the waveform projecting upward and the waveform projecting downward.

The analysis method according to the present embodiment includes the irradiation step of irradiating, with the irradiation light 20a, the sample analysis disc 70 having the surface to which the detection target substances 63 and the particles 64 bound to the detection target substances 63 are fixed. The analysis method includes the generation step of receiving the reflection light of the irradiation light 20a from the sample analysis disc 70 to generate the light reception level signal JS. The analysis method includes the count step of determining and counting the pulse as a pulse derived from the plural detection target substances 63 when fulfilling the following conditions. The pulse included in the light reception level signal JS includes the first extreme value point PV1, the second extreme value point PV2, and the third extreme value point PM1, in which the third extreme value point PM1 is present between the first extreme value point PV1 and the second extreme value point PV2 in the pulse width direction of the pulse. The third extreme value point PM1 is present between the first extreme value point PV1 and the threshold Vth in the pulse amplitude direction of the pulse. The first extreme value point PV1 and the second extreme value point PV2 are the extreme value points of one of the waveform projecting upward and the waveform projecting downward, and the third extreme value point PM1 is the extreme value point of the other one of the waveform projecting upward and the waveform projecting downward.

The controller 9 thus can specify the particles 64 that label the detection target substances 63 according to the number of the extreme value points in the light reception level signal JS generated by the scanning of the isolated particle 64 or the two particles 64 adjacent to each other, and the comparison results of the time widths between the respective extreme value points, so as to count the number of the particles 64 accordingly.

This is also applicable to the case in which the three or more particles 64 are present adjacent to each other. For example, as illustrated in FIG. 9, the light reception level signal JS generated by the scanning of the three particles 64 adjacent to each other includes the extreme value point PV1 to the extreme value point PV3, and the extreme value point PM1 and the extreme value point PM2. The respective widths between the extreme value point PM1 and the adjacent extreme value point PV1 in the pulse width direction and between the extreme value point PM1 and the adjacent extreme value point PV3 in the pulse width direction are substantially the same. Similarly, the respective widths between the extreme value point PM2 and the adjacent extreme value point PV3 in the pulse width direction and between the extreme value point PM2 and the adjacent extreme value point PV2 in the pulse width direction are substantially the same. Namely, the light reception level signal JS is presumed to include the two extreme value points, including the extreme value point PM1, having the same characteristics as the extreme value point PM1 between the extreme value point PV1 and the extreme value point PV2. Comparing Td1 to Td3 and Tu1 to Tu3 that are the time widths between the respective extreme value points, can specify the particles 64 that label the detection target substances 63 so as to count the number of the particles 64.

Namely, the controller 9 may determine and count the pulse included in the light reception level signal JS as the pulse derived from the (n+2) number of the detection target substances 63 when the pulse included in the light reception level signal JS further includes the n-number (n is an integer of 0 or greater) of any other extreme value point having the same characteristics (including a polarity) as the third extreme value point PM1, and when the pulse fulfils the following conditions. The conditions include a case in which the other extreme value point is present between the first extreme value point PV1 and the second extreme value point PV2 in the pulse width direction of the pulse, and the other extreme value point is present between the first extreme value point PM1 and the threshold Vth in the pulse amplitude direction of the pulse. The conditions further include a case in which the other extreme value point is the extreme value point of the other waveform, which projects in the same direction as the third extreme value point PM1. The other extreme value point differs from the first extreme value point PV1, the second extreme value point PV2, or the third extreme value point PM1, and is the fifth extreme value point PM2 as illustrated in FIG. 9, for example. In particular, the pulse included in the light reception level signal JS may further include the n-number (n is an integer of 0 or greater) of any other extreme value point between the third extreme value point PM1 and the second extreme value point PV2 in the pulse width direction of the pulse. The number of n may be an integer of 1 or greater. When n is an integer of 1 or greater, the controller 9 can count the pulse derived from the three or more particles.

While the present embodiment has been described above by reference to the examples, it should be understood that the present embodiment is not intended to be limited to the descriptions above, and various modifications and improvements will be apparent to those skilled in the art.

For example, while the analysis device 1 according to the present embodiment has been illustrated above with the case in which the sample analysis disc 70 is placed on the turntable 2 such that the respective reaction regions 66 face downward, the analysis device 1 is not limited to this case, and may have a configuration in which the respective reaction regions 66 face upward.

For example, the analysis method may execute the detection of the respective extreme value points and the measurement of time between the respective extreme value points first, and execute the processing of determining the time width later.

The signal intensity Vb is related to the magnetic characteristics of the particles 64. For example, when the particles 64 contain a large amount of magnetic substance, the signal intensity Vb may be increased. When the magnetic characteristics of the particles 64 have a range of variation, the signal intensity Vb is not set to a fixed value, but the respective extreme value points may be detected while an intensity width is defined in a range of Vb1 or greater and Vb2 or smaller The present discloser can provide the analysis device and the analysis method having high quantitative performance upon detecting particles present close to each other.

What is claimed is:

1. An analysis device, comprising:
   an optical pickup configured to irradiate, with an irradiation light, a sample analysis disc having a surface to which detection target substances and particles bound to the detection target substances are fixed, and receive a reflection light of the irradiation light from the sample analysis disc to generate a light reception level signal; and
   a controller configured to detect a fall when a signal intensity of the light reception level signal is a first predetermined threshold or smaller,
   wherein the controller is further configured to measure a first decreasing time that the signal intensity of the light reception level signal takes to decrease from the first predetermined threshold to a first extreme value point at which the signal intensity shifts from a fall to a rise,
   wherein the controller is further configured to measure a first increasing time that the signal intensity of the light reception level signal takes to increase from the first extreme value point to a third extreme value point at which the signal intensity shifts from a rise to a fall,
   wherein the controller is further configured to measure a second decreasing time that the signal intensity of the light reception level signal takes to decrease from the third extreme value point to a second extreme value point at which the signal intensity shifts from a fall to a rise,
   wherein the controller is further configured to measure a second increasing time that the signal intensity of the light reception level signal takes to increase from the second extreme value point to the first predetermined threshold,
   wherein the controller is further configured to determine whether the first increasing time and the second decreasing time conform to each other such that the first increasing time has a value within a predefined range of a value of the second decreasing time, and the first decreasing time and the second increasing time conform to each other such that the first decreasing time has a value within a predefined range of a value of the second increasing time, and
   wherein the controller is further configured to count a pulse derived from the particles as plural particles when the controller determines the first increasing time and the second decreasing time, and the first decreasing time and the second increasing time, conform to each other, the controller not counting the pulse derived from the particles as plural particles when the controller determines that the first increasing time and the second decreasing time, and the first decreasing time and the second increasing time, do not conform to each other.

2. The analysis device according to claim 1, wherein the third extreme value point is present adjacent to the first extreme value point.

3. The analysis device according to claim 2, wherein a difference between a first width between the first extreme value point and the third extreme value point and a second width between the third extreme value point and an extreme value point adjacent to the third extreme value point on an opposite side of the first extreme value point in the pulse width direction is 15% or less of either the first width or the second width having a greater value.

4. The analysis device according to claim 1, wherein:
   the first extreme value point is an extreme value point present at a position closest to a first intersection of the pulse with the threshold toward the first extreme value point with respect to the third extreme value point; and
   the second extreme value point is an extreme value point present at a position closest to a second intersection of the pulse with the threshold on an opposite side of the first extreme value point with respect to the third extreme value point.

5. The analysis device according to claim 4, wherein a difference between a third width between the first intersection and the first extreme value point and a fourth width between the second intersection and the second extreme value point in the pulse width direction is 15% or less of either the third width or the fourth width having a greater value.

6. An analysis method, comprising:
   an irradiation step of irradiating, with an irradiation light, a sample analysis disc having a surface to which detection target substances and particles bound to the detection target substances are fixed;

a generation step of receiving a reflection light of the irradiation light from the sample analysis disc to generate a light reception level signal;

a detecting step of detecting a fall when a signal intensity of the light reception level signal is a first predetermined threshold or smaller;

a first measuring step of measuring a first decreasing time that the signal intensity of the light reception level signal takes to decrease from the first predetermined threshold to a first extreme value point at which the signal intensity shifts from a fall to a rise;

a second measuring step of measuring a first increasing time that the signal intensity of the light reception level signal takes to increase from the first extreme value point to a third extreme value point at which the signal intensity shifts from a rise to a fall;

a third measuring step of measuring a second decreasing time that the signal intensity of the light reception level signal takes to decrease from the third extreme value point to a second extreme value point at which the signal intensity shifts from a fall to a rise;

a fourth measuring step of measuring a second increasing time that the signal intensity of the light reception level signal takes to increase from the second extreme value point to the first predetermined threshold; and a count step of counting a pulse derived from the particles as plural particles when the first increasing time and the second decreasing time conform to each other such that the first increasing time has a value within a predefined range of a value of the second decreasing time, and the first decreasing time and the second increasing time conform to each other such that the first decreasing time has a value within a predefined range of a value of the second increasing time, and not counting the pulse derived from the particles as plural particles when the first increasing time and the second decreasing time, and the first decreasing time and the second increasing time, do not conform to each other.

\* \* \* \* \*